(12) United States Patent
Howe, Jr. et al.

(10) Patent No.: US 8,534,283 B2
(45) Date of Patent: Sep. 17, 2013

(54) PEEP VALVE WITH FILTER

(75) Inventors: George E. Howe, Jr., Largo, FL (US); Brian Maxfield, Clearwater, FL (US); Jeffrey B. Ratner, Pinellas Park, FL (US)

(73) Assignee: Mercury Enterprises, Inc., Clearwater, FL (US)

( * ) Notice: Subject to any disclaimer, the term of this patent is extended or adjusted under 35 U.S.C. 154(b) by 376 days.

(21) Appl. No.: 12/838,571

(22) Filed: Jul. 19, 2010

(65) Prior Publication Data
US 2012/0012111 A1  Jan. 19, 2012

(51) Int. Cl.
*A62B 9/02* (2006.01)
*A62B 7/04* (2006.01)
*A62B 7/10* (2006.01)
*A62B 19/00* (2006.01)
*A62B 23/02* (2006.01)
*F16K 31/26* (2006.01)

(52) U.S. Cl.
USPC ............ 128/205.24; 128/204.26; 128/205.12

(58) Field of Classification Search
USPC ............ 128/204.06, 204.08, 204.21, 204.27, 128/204.28, 205.13–17, 205.24, 205.25, 128/205.27, 205.29, 206.12, 206.15, 207.14, 128/207.18, 201.13, 204.18, 204.26; 137/512.3, 137/524
See application file for complete search history.

(56) References Cited

U.S. PATENT DOCUMENTS

| | | | |
|---|---|---|---|
| 4,323,064 A | | 4/1982 | Hoenig |
| 4,436,090 A | * | 3/1984 | Darling .................... 128/204.26 |
| 4,867,153 A | | 9/1989 | Lorenzen |
| 4,951,661 A | | 8/1990 | Sladek |
| 5,333,607 A | | 8/1994 | Kee |
| 5,433,195 A | | 7/1995 | Kee |
| 5,445,141 A | | 8/1995 | Kee |
| 5,628,306 A | | 5/1997 | Kee |
| 6,135,108 A | | 10/2000 | Hoenig |
| 6,516,803 B1 | | 2/2003 | Enzinger |
| 7,341,059 B2 | | 3/2008 | Moody |
| 2007/0221221 A1 | | 9/2007 | Cooke et al. |
| 2008/0223361 A1 | | 9/2008 | Nieuwstad |
| 2008/0229929 A1 | * | 9/2008 | Marcoon ........................ 96/296 |
| 2009/0250060 A1 | * | 10/2009 | Hacke et al. ............. 128/205.12 |
| 2010/0199991 A1 | * | 8/2010 | Koledin .................... 128/205.12 |

FOREIGN PATENT DOCUMENTS

WO       2008070989       6/2008

* cited by examiner

*Primary Examiner* — Jackie Ho
*Assistant Examiner* — Mark K Han
(74) *Attorney, Agent, or Firm* — Larson & Larson, P.A.; Frank Liebenow; Justin P. Miller

(57) ABSTRACT

An application for a PEEP valve includes a filter media in the air flow between a patient interface and exit vent(s). The patient interface is connected to a patient airway system and the exit vents exhaust exhalation gasses into the atmosphere. The filter prevents or reduces the passage of microbes from the patient's exhalation gasses into the atmosphere. The PEEP valve provides positive gas pressure to a patient's lungs, requiring a predetermined exhalation gas pressure to be exceeded before releasing exhalation gasses into the atmosphere.

20 Claims, 6 Drawing Sheets

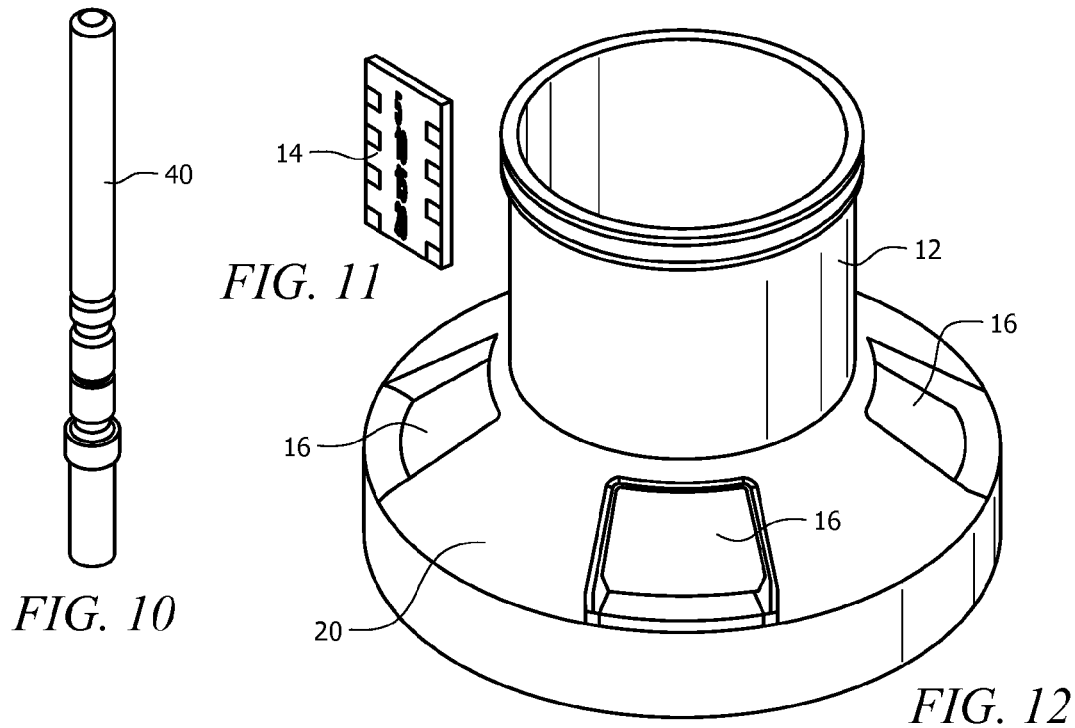
FIG. 10
FIG. 11
FIG. 12
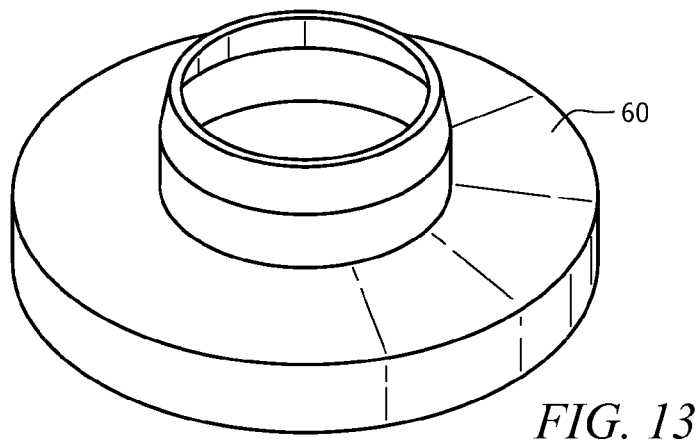
FIG. 13
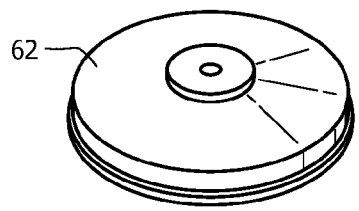
FIG. 14

PEEP VALVE WITH FILTER

FIELD

This invention relates to the field of medicine and more particularly to a device that provides positive end expiatory pressure valve and has an integral filter.

BACKGROUND

This invention relates to a positive end expiratory pressure valve (referred to as a PEEP valve). In the current art, PEEP valves usually include a hollow cylinder or port providing a gas flow path for exhalation gas from a patient to which the PEEP valve is connected. The PEEP valve requires an adjustable exhalation gas pressure before it releases exhalation gasses into the atmosphere, thereby maintaining pressure in a patient's lungs.

Numerous devices are known to the art which provide flow paths for gasses such as air, oxygen, anesthesia gas, and the like. Numerous medical apparatus are also known to the art which provide a gas flow path for exhalation gas from a patient's lungs such as air, oxygen, anesthesia gas, etc.

PEEP valves, as known to the art, are used to maintain a predetermined pressure level in the lungs of a patient who is being ventilated with oxygen, air or anesthetized by an anesthesia gas. Typical PEEP valves includes a spring biased relief valve which remains closed and prevents the patient from exhaling until the pressure of the patient's exhalation gas exceeds the force of the spring after which the valve opens and the patient's exhalation gas is exhausted through a exit port on the PEEP valve and into the atmosphere. As the patient continues to exhale, the pressure of the exhalation gas decreases until it reaches the force set by the spring biased relief valve and the valve closes thereby preventing the further flow of exhalation gas from the patient's lungs. The gas remaining in the patient's lungs which otherwise would be exhaled, remains in the patient's lungs at a pressure equal to, or at least substantially equal to, the pressure setting of the spring. It is advantageous for a patient being ventilated or anesthetized to have at least some pressure remaining in their lungs and to prevent the patient's lungs from being totally evacuated during exhalation. The maintenance of such gas pressure is believed to have a salutary effect on the sacks or alveoli of the patient's lungs.

FIG. 1 of U.S. Pat. No. 6,135,108 to Richard Hoenig shows a patient being ventilated by air or oxygen from a suitable source. This patent is hereby included by reference. Gas enters the flowmeter, flows through the heated humidifier, through tubing (12), through a T-piece, and into the endotracheal tube with which the patient is intubated. When the patient exhales, the exhalation gas from the patient's lungs flows through the endotracheal tube, the T-piece and into the PEEP valve. When pressure exceeds the spring force of the PEEP valve, the patient's exhalation gas exits through the PEEP valve's exit port and into the ambient air in the patient's room.

Existing PEEP valves allow exhalation gasses to exit into the atmosphere around the patient. In many hospital situations, the patient has a communicable disease ranging from the common cold to bacterial pneumonia. As the patient exhales, pathogens, microbes or microorganisms are released, for example, in aerosolized droplets. These pathogens exit the PEEP valve exit port when the patient exhales as described above. Many pathogens will cause an infectious disease in a healthy adult, but those pathogens and a host of other pathogens cause an infectious disease in a person with depressed resistance (e.g. a patient suffering from another disease such as HIV or cancer). The later are classified as opportunistic pathogens. Being that many other patients in a hospital or even in the same room as the person using the PEEP valve potentially have depressed resistance; they are more susceptible to acquiring such a disease from the person using the PEEP valve. Likewise, for certain diseases and pathogens, caretakers are also susceptible to such microbes and pathogens.

In the past, recognizing the dangers of allowing such pathogens to leave the patient's lungs and into the atmosphere, medical facilities have attached filters between the PEEP valve and the patient airway. This reduces pathogen emission into the atmosphere, but requires a separate filter device inserted into the flow path. A separate filter device adds costs for the housing and connections, creates a larger, more cumbersome connection and increases the chances of a disconnected flow path.

What is needed is a PEEP valve with integral filter that prevents or reduces the emission of pathogens into the air surrounding the patient using such device.

SUMMARY

A PEEP valve is disclosed that provides positive gas pressure to a patient's lungs, requiring a predetermined exhalation gas pressure to be exceeded before releasing exhalation gasses into the atmosphere. The PEEP valve has an integral filter in the air flow between a patient interface and exit vents. The patient interface is connected to a patient airway system and the exit vents exhaust exhalation gasses into the atmosphere. The filter prevents or reduces the passage of microbes from the patient's exhalation gasses into the atmosphere.

In one embodiment, a PEEP valve for maintaining pressurized gas in a patient's lungs is disclosed. The PEEP valve includes a patient interface and a valve biased by a spring to inhibit passage of exhalation gasses from the patient interface and out of vents formed in the PEEP valve until a pressure of the exhalation gasses exceeds a force of the spring. A biological filter is positioned between the patient interface and the vents. The exhalation gasses pass through the biological filter before exiting through the vents, thereby preventing or reducing the passage of microbes into the atmosphere.

In another embodiment, a method of reducing emissions of microbes from a patient into the atmosphere is disclosed including connecting a PEEP valve to an airway system connected to a patient to pressurize exhalation gasses of the patient. The PEEP valve has a patient interface for connecting to the airway system with a valve that is biased by a spring to inhibit passage of the exhalation gasses from the patient interface and out of vents formed in the PEEP valve until a pressure of the exhalation gasses exceeds a force of the spring. The PEEP valve has a biological filter positioned between the patient interface and the vents. The exhalation gasses pass through the biological filter before exiting through the vents. The method includes the patient exhaling. When the pressure of the exhalation gasses exceeds the force of the spring, the valve opens and the exhalation gasses pass through the biological filter and out of the PEEP valve and through the vents. Microbes in the exhalation gasses are retained by the biological filter.

In another embodiment, a PEEP valve for maintaining pressurized gas in a patient's lungs is disclosed including, an enclosure having a patient interface with a biological filter interfaced to the patient interface. The biological filter allows passage of exhalation gasses from the patient interface while preventing the passage of at least some microbes from the patient interface. A valve is biased by a first end of a spring. The valve inhibits passage of the exhalation gasses from the patient interface until a pressure of the exhalation gasses exceeds a force of the spring. A knob is interfaced to the enclosure by threads. The knob is also interfaced to a second end of the spring such that tightening of the knob compresses the spring, increasing the force of the spring against the valve.

BRIEF DESCRIPTION OF THE DRAWINGS

The invention can be best understood by those having ordinary skill in the art by reference to the following detailed description when considered in conjunction with the accompanying drawings in which:

FIGS. 4-21 illustrate individual components of the PEEP valve with integrated filter.

DETAILED DESCRIPTION

Figure 1:
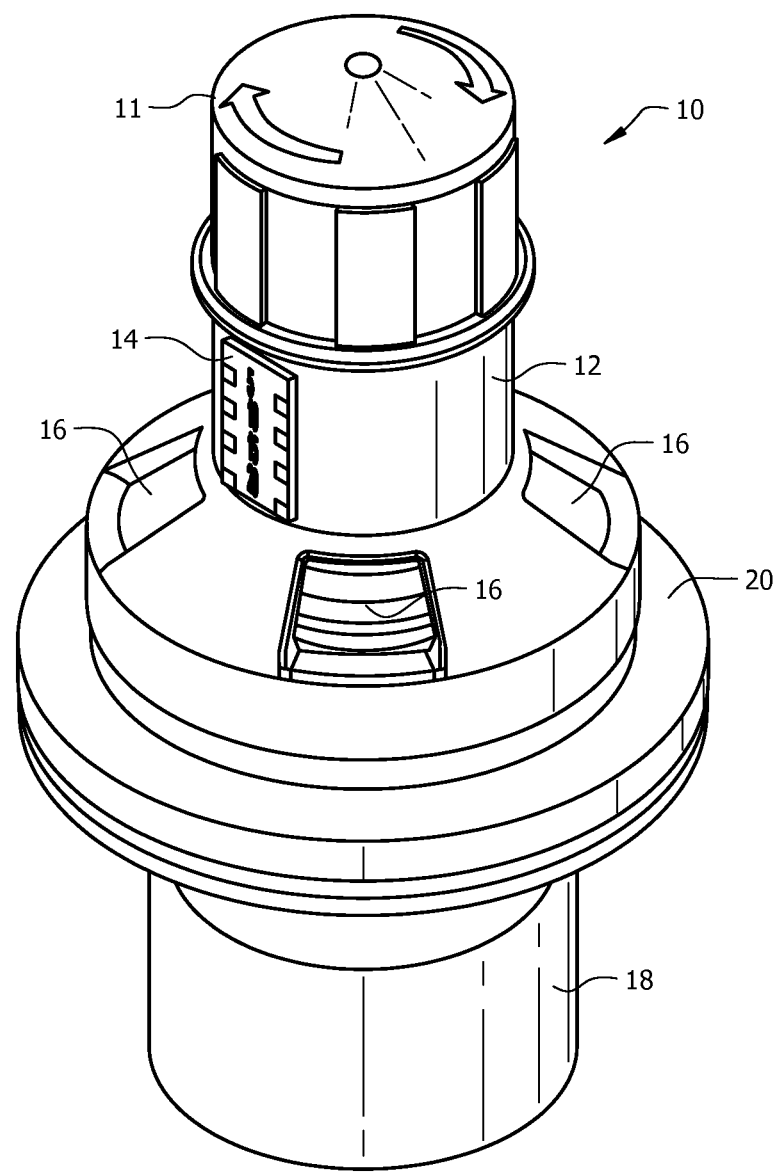
FIG. 1 illustrates a perspective view of a PEEP valve with an integrated filter.

Reference will now be made in detail to the presently preferred embodiments of the invention, examples of which are illustrated in the accompanying drawings. Throughout the following detailed description, the same reference numerals refer to the same elements in all figures.

Referring to FIG. 1, a perspective view of a PEEP valve 10 with an integrated filter will be described. From the outside, the PEEP valve 10 with integral filter looks similar to other PEEP valves having a spring tension adjustment knob 11 that is screw fitted to the knob base 12 such that, as the spring tension adjustment knob 11 is turned in one direction, it tightens the tension of one or more adjustment springs 36/38 (see FIGS. 2, 3, 8 and 9) and as the tension adjustment knob 11 is turned in the opposite direction, it loosens the tension of the adjustment spring(s) 36/38. An indicator marker 14 is attached or molded into the knob base 12 to show the approximate pressure setting of the adjustment spring(s) 36/38. A base member 20 has a one or more exhaust port openings or vent windows 16, whereby exhalation gasses exit when the tension of the adjustment spring(s) 36/38 is exceeded. An interface port 18 is connected to the airway system (not shown), typically through an exhalation port or a T-connector (not shown).

Figure 2:
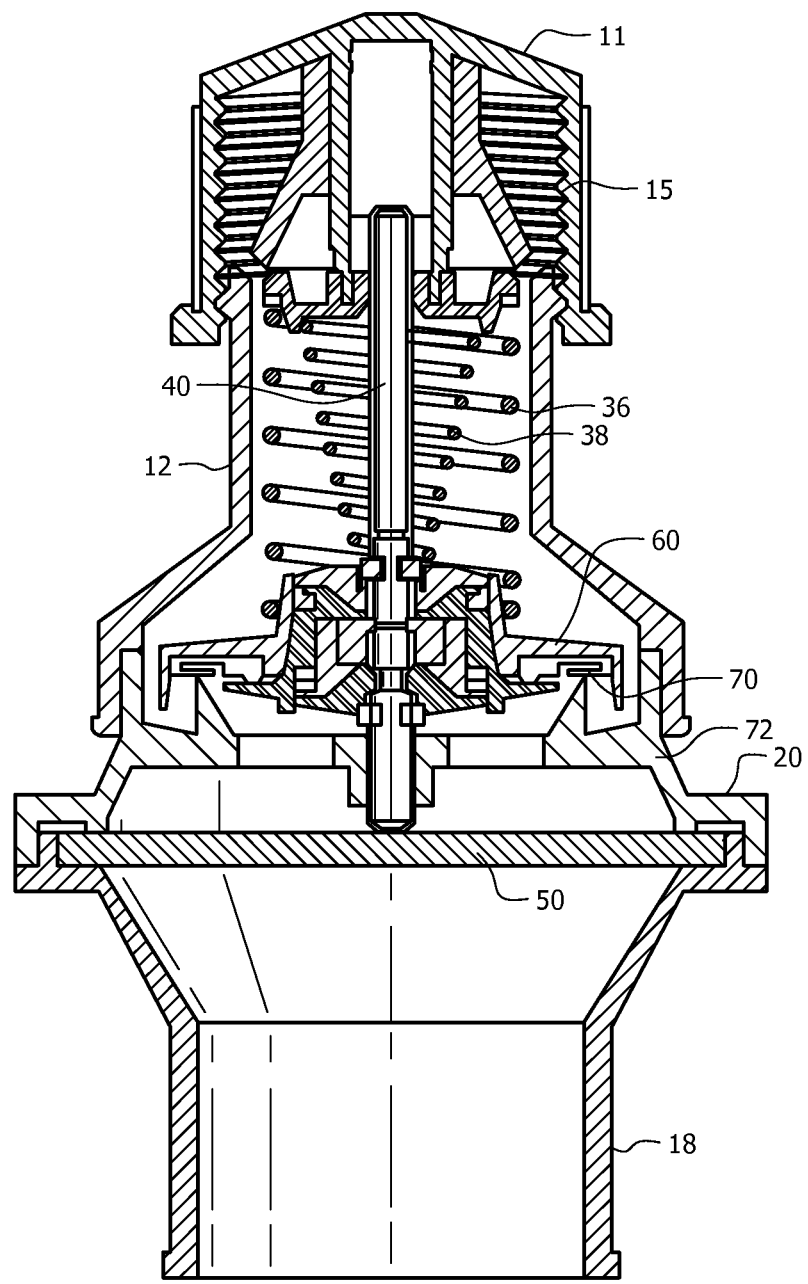
FIG. 2 illustrates a sectional view of a PEEP valve with an integrated filter.

Referring to FIG. 2, a sectional view of a PEEP valve 10 with an integrated filter media 50 will be described. The spring tension adjustment knob 11 is screw fitted to the knob base 12 with threads 15. As the spring tension adjustment knob 11 is turned in one direction, it tightens the tension of springs 36/38 and as the tension adjustment knob 11 is turned in the opposite direction, it loosens the tension of the spring 36/38. Above the interface port 18 is a filter media 50 that blocks pathogens or biological hazards emanating from the patient, passing through the airway system (not shown) and into the interface port 18. Biological filters are known in the industry, for example, those used in face masks, electrostatic filters, etc. Electrostatic filters include a presence of an electrostatic charge on the particles of the fabric, leading to an increase in capture of small particles.

It is anticipated that, in some filter media 50, anti-microbial materials such as silver nitride are present to neutralize the pathogens, further reducing the possibility of release into the atmosphere and introduction to people in the area.

Figure 3:
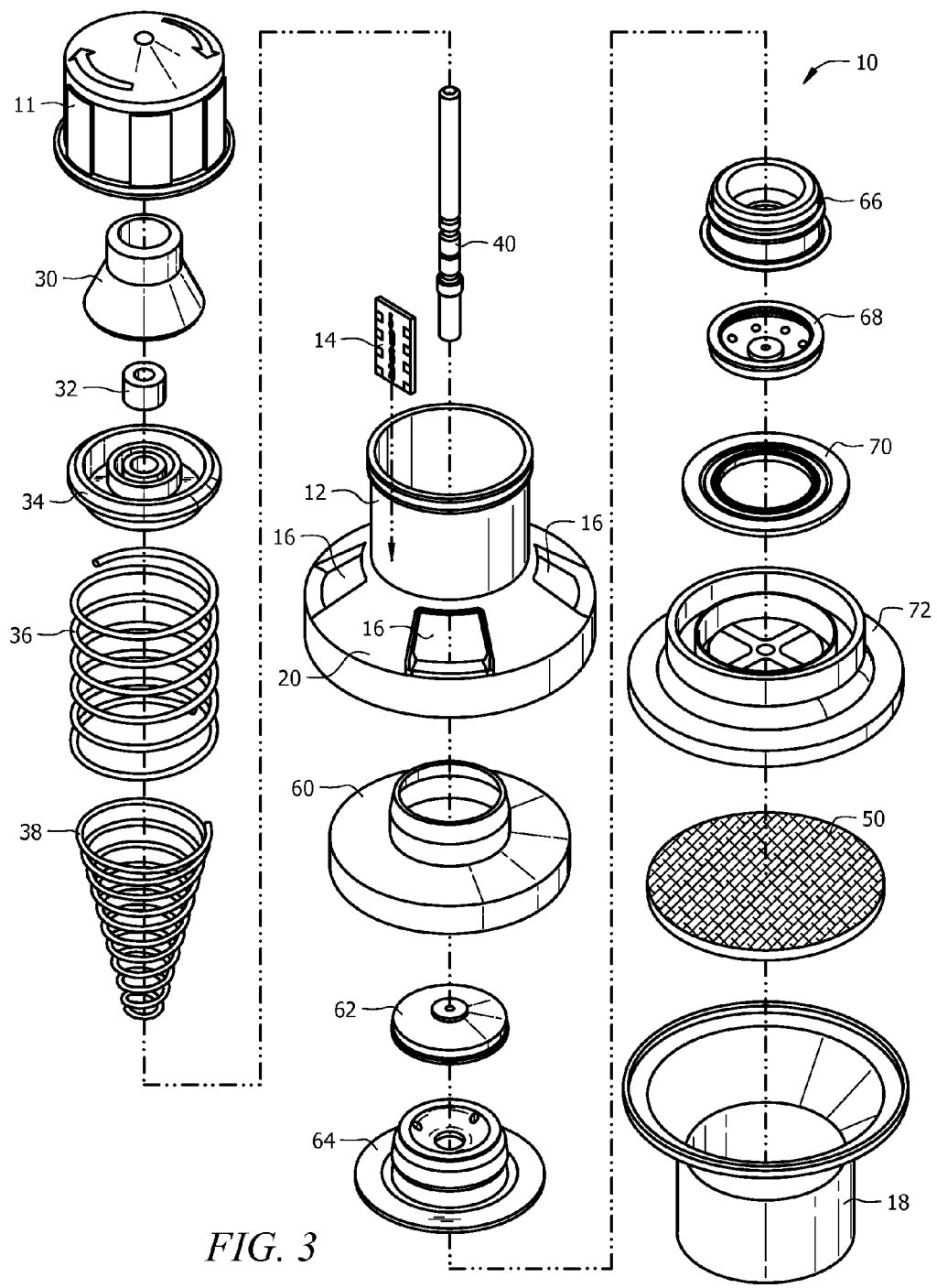
FIG. 3 illustrates an exploded view of a PEEP valve with an integrated filter.

Referring to FIG. 3, an exploded view of a PEEP valve 10 with an integrated filter will be described. The structure and components shown are exemplary and there are many ways to fabricate and manufacture a fluid valve that exhausts a person's exhalation gas after a pre-determined and preferably settable exhalation gas pressure is reached. The general structure is shown as an enablement of a PEEP valve 10 showing one way to implement a filter media 50 within such a PEEP valve 10. Other structures with filter media 50 are anticipated and included herewithin. Likewise, the location of the filter media 50 is a preferred location, but other locations are also anticipated such as within the vent windows 16, etc.

The PEEP valve 10 shown has a threaded adjustment knob 11 that is threaded onto the knob base 12. Tightening of the knob 11 compresses the spring(s) 36/38, requiring a greater exhalation gas pressure to open the valve seal 70 that is normally seated on the valve seat 72, thereby releasing the exhalation gas through the vent windows 16. The knob is fitted on a shaft 40 a stopper 30, shaft cap 32 and spring stop 34 which support an upper end of the springs 36/38. The bottom of the adjustment spring 36 seats against the valve cap 60, providing pressure to the valve seal 70 against the valve seat 72. When the patient exhales, once the exhalation gas pressure exceeds the pressure of the adjustment spring 36, the valve seal 70 lifts from the valve seat 72 and exhalation gasses exit though the vent windows 16.

In some embodiments, a label 14 or marking 14 indicates the position of the knob 11 and hence, the exhalation gas pressure setting. In this example, various other components are present including a valve cap 60, a large grease cap 64, a small grease cap 66, an upper retainer 62, and a lower retainer 68. These components are present in some exemplary PEEP valves 10 to improve operation and reduce chatter noise when the user exhales. In this embodiment, a filter media 50 is situated between the valve seat 72 and the filter case/patient interface 18. It is anticipated that the filter media 50 be located in other locations of the PEEP valve 10 as long as gas flows through the filter before exiting the PEEP valve 10. The filter media 50 allows exhalation gasses to enter the PEEP valve 10 from the patient interface 18 and, once the preset pressure is reached, the exhalation gasses exit the vent windows 16. The filter prevents certain biological agents from passing from the patient interface 18 and out through the vent windows 16. The simplest filter media 50 would be a fiber filter similar to those used in hospital face masks, though many different types of filters 50 are anticipated. It is anticipated that some classes of PEEP valves 10 have one type of filter media 50 while other classes of PEEP valves 10 have a different type of filter; each type is used for a patient with a different disease. For example, one class of PEEP valves have filters selected for patients with HIV and another class have filters selected for patients with pneumonia.

In some embodiments, the filter media 50 includes an antimicrobial substance such as silver nitrite. Filters 50 that include antimicrobial substances not only prevent the microbes from exiting the PEEP valve 10 and into the atmosphere, the antimicrobial substances also neutralize the microbes. This is important to reduce emissions of microbes once the PEEP valve 10 is disconnected from the patient airway system, at which time, it is possible that microbes lodged on the patient side of the filter media 50 will escape into the atmosphere. The antimicrobial substance(s) will neutralize the microbes before they have a chance to escape into the atmosphere.

Figure 4:
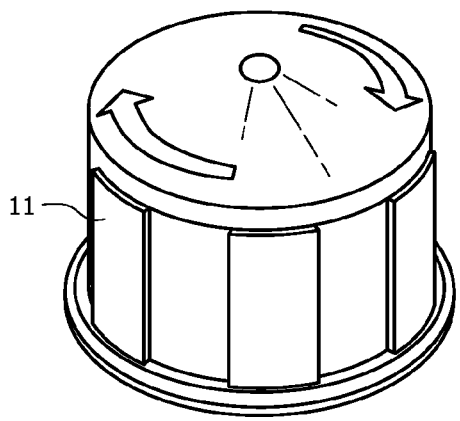
Figure 5:
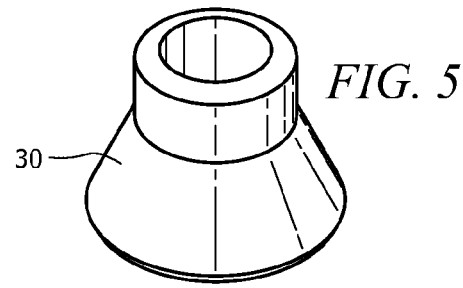
Figure 6:
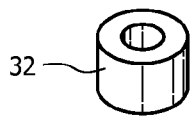
Figure 7:
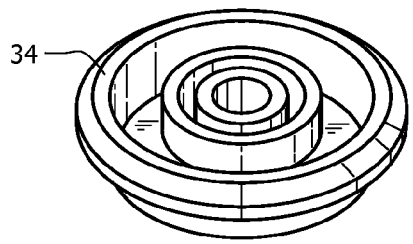
Figure 8:
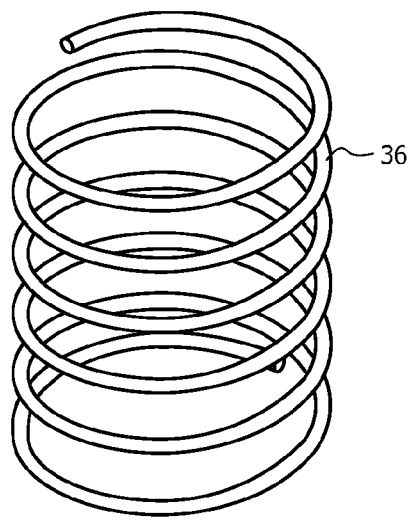
Figure 9:
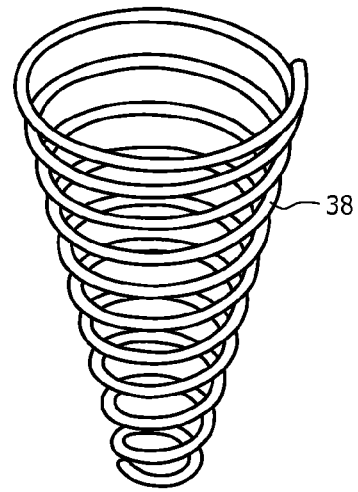
Figure 15:
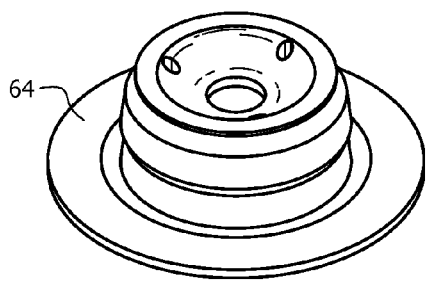
Figure 19:
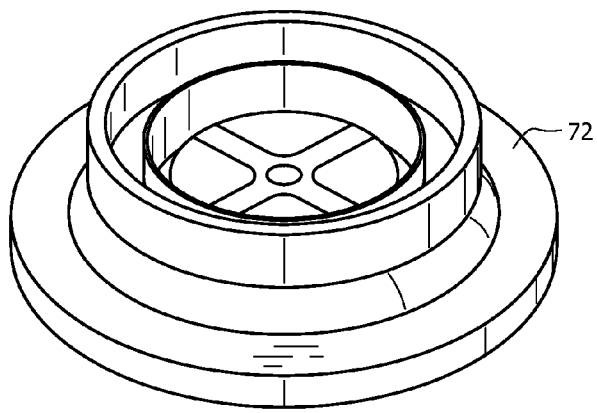
Figure 16:
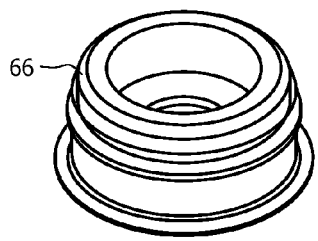
Figure 20:
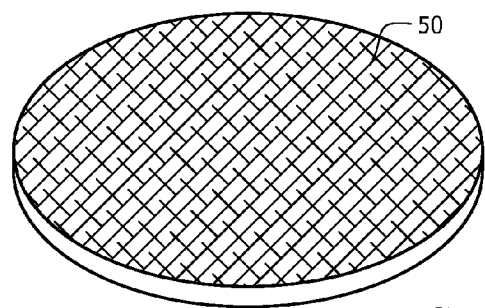
Figure 17:
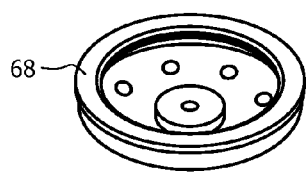
Figure 18:
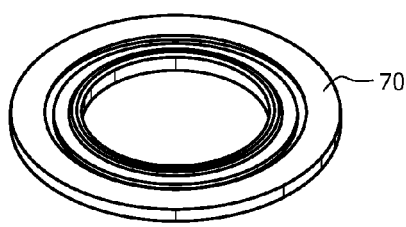
Figure 21:
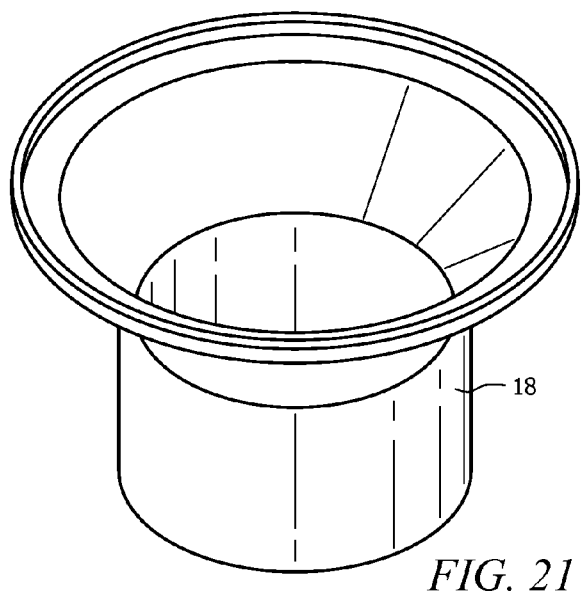

Referring to FIGS. 4-21, individual components of the PEEP valve with integrated filter will be described. FIG. 4 shows the knob 11. FIG. 5 shows the stopper 30. FIG. 6 shows the shaft cap 32. FIG. 7 shows the spring stop 34. FIG. 8 shows the adjustment spring 36. FIG. 9 shows the cone spring 38, FIG. 10 shows the shaft 40. FIG. 11 shows the label 14. FIG. 12 shows the top cover 20 with knob base 12 and vent windows 16. FIG. 13 shows the valve cap 60. FIG. 14 shows the upper retainer 62. FIG. 15 shows the large grease cap 64. FIG. 16 shows the small grease cap 66. FIG. 17 shows the lower retainer 68. FIG. 18 shows the valve seal 70. FIG. 19 shows the valve seat 72. FIG. 20 shows the filter media 50. Finally, FIG. 21 shows the filter case/patient interface 18.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A positive end expiratory pressure valve for maintaining pressurized gas in a patient's lungs, the positive end expiratory pressure valve comprising:
   a base member having a patient interface;
   a valve biased by a spring to inhibit passage of exhalation gases from the patient interface and out of one or more vents formed in the base member until a pressure of the exhalation gases exceeds a force of the spring; and
   a biological filter within the base member and positioned between the patient interface and the vents, the exhalation gases passing through the biological filter before exiting through the vents.

2. The positive end expiratory pressure valve of claim 1, further comprising an adjustment knob, the adjustment knob linked to the spring, such that tightening of the adjustment knob results in compression of the spring, thereby increasing the force of the spring.

3. The positive end expiratory pressure valve of claim 1, wherein the biological filter includes an antimicrobial, wherein the antimicrobial neutralizes biological agents that are trapped in the biological filter.

4. The positive end expiratory pressure valve of claim 3, wherein the antimicrobial is silver nitrate.

5. The positive end expiratory pressure valve of claim 3, wherein the antimicrobial is a silver-based material.

6. The positive end expiratory pressure valve of claim 1, wherein the biological filter is an electrostatic material.

7. A method of reducing emissions of microbes from a patient into the atmosphere, the method comprising:
   connecting a positive end expiratory pressure valve to an airway system connected to a patient to pressurize exhalation gases of the patient, the positive end expiratory pressure valve having:
      a base member having a patient interface;
      a valve biased by a spring to inhibit passage of the exhalation gases from the patient interface and out of one or more vents formed in the positive end expiratory pressure valve until a pressure of the exhalation gases exceeds a force of the spring;
      a biological filter within the base member and positioned between the patient interface and the vents, the exhalation gases passing through the biological filter before exiting through the vents;
   the patient exhaling; and
   when the pressure of the exhalation gases exceeds the force of the spring, opening of the valve and the exhalation gases pass through the biological filter and out of the positive end expiratory pressure valve through the vents, microbes in the exhalation gases being retained by the biological filter.

8. The method of claim 7, further comprising the step of: when the pressure of the exhalation gases abates to less than the force of the spring, closing of the valve.

9. The method of claim 7, further comprising an adjustment knob, the adjustment knob linked to the spring, the method including tightening of the adjustment knob thereby increasing the force of the spring.

10. The method of claim 7, wherein the biological filter includes an antimicrobial, the antimicrobial neutralizing biological agents that are trapped in the biological filter.

11. The method of claim 10, wherein the antimicrobial is silver nitrate.

12. The method of claim 10, wherein the antimicrobial is a silver-based material.

13. The method of claim 7, wherein the biological filter is a tightly woven material.

14. The method of claim 7, wherein the biological filter is an electrostatic material.

15. A positive end expiratory pressure valve for maintaining pressurized gas in a patient's lungs, the positive end expiratory pressure valve comprising:
   an enclosure;
   a patient interface on the enclosure;
   a valve within the enclosure, the valve biased by a first end of a spring, the valve configured to inhibit passage of the exhalation gases from the patient interface through a biological filter and out vents in the enclosure until a pressure of the exhalation gases exceeds a force of the spring; and
   a knob interfaced to the enclosure by threads, the knob interfaced to a second end of the spring such that tightening of the knob compresses the spring, thereby increasing the force of the spring against the valve; and
   wherein the biological filter is within the enclosure, and whereas the biological filter allows passage of exhalation gases from the patient interface and the biological filter prevents the passage of at least some microbes from the patient interface through the biological filter.

16. The positive end expiratory pressure valve of claim 15, wherein the biological filter includes an antimicrobial, wherein the antimicrobial neutralizes biological agents that are trapped in the biological filter.

17. The positive end expiratory pressure valve of claim 16, wherein the antimicrobial is silver nitrate.

18. The positive end expiratory pressure valve of claim 16, wherein the antimicrobial is a silver-based material.

19. The positive end expiratory pressure valve of claim 15, wherein the biological filter is a tightly woven material.

20. The positive end expiratory pressure valve of claim 15, wherein the biological filter is an electrostatic material.

* * * * *